United States Patent [19]

Hagiwara et al.

[11] Patent Number: 5,024,650
[45] Date of Patent: Jun. 18, 1991

[54] STRESS DISSOLVING REFRESHMENT SYSTEM

[75] Inventors: Hiroshi Hagiwara, Katano; Kazunori Araki, Kita Katsuragi; Akihiro Michimori, Nishinomiya, all of Japan

[73] Assignee: Matsushita Electric Works, Ltd., Japan

[21] Appl. No.: 475,990

[22] Filed: Jan. 6, 1990

[30] Foreign Application Priority Data

Feb. 15, 1989 [JP] Japan .................................. 1-35224
Feb. 15, 1989 [JP] Japan .................................. 1-35225
Jul. 15, 1989 [JP] Japan .................................. 1-182793

[51] Int. Cl.$^5$ ............................................ A61M 21/00
[52] U.S. Cl. ................................. 600/26; 128/33; 128/371; 128/377; 128/24.1
[58] Field of Search ................... 600/26, 27, 28; 128/24.1, 33, 362, 371, 373, 375, 376, 377, 905

[56] References Cited

U.S. PATENT DOCUMENTS

| | | | |
|---|---|---|---|
| 3,826,250 | 7/1974 | Adams | 600/28 |
| 4,047,377 | 9/1977 | Banks, Jr. | 600/28 |
| 4,315,502 | 2/1982 | Gorges | 600/27 |
| 4,640,266 | 2/1987 | Levy | 600/27 |
| 4,893,615 | 1/1990 | Khabirova | 128/24.1 |

FOREIGN PATENT DOCUMENTS

| | | | |
|---|---|---|---|
| 2040818 | 2/1972 | Fed. Rep. of Germany | 600/27 |
| 61-220653 | 9/1986 | Japan . | |
| 62-38162 | 2/1987 | Japan . | |
| 62-87168 | 4/1987 | Japan . | |
| 63-283641 | 11/1988 | Japan . | |

Primary Examiner—William E. Kamm
Attorney, Agent, or Firm—Leydig, Voit & Mayer

[57] ABSTRACT

A stress dissolving refreshment system causes a relaxed state induction means actuated during a relaxing period, thereafter a refresh stimulus means actuated to generate a weak stimulation during a disillusion period in which the level of consciousness of the user is gradually elevated, and then the refresh stimulus means further actuated to generate a strong stimulation during a refreshing period in which the level of the user's consciousness is elevated to a level good enough for allowing the user to return to normal working, whereby the consciousness level of the user is quickly elevated after being relaxed, so as to effectively attain the refreshment.

24 Claims, 9 Drawing Sheets

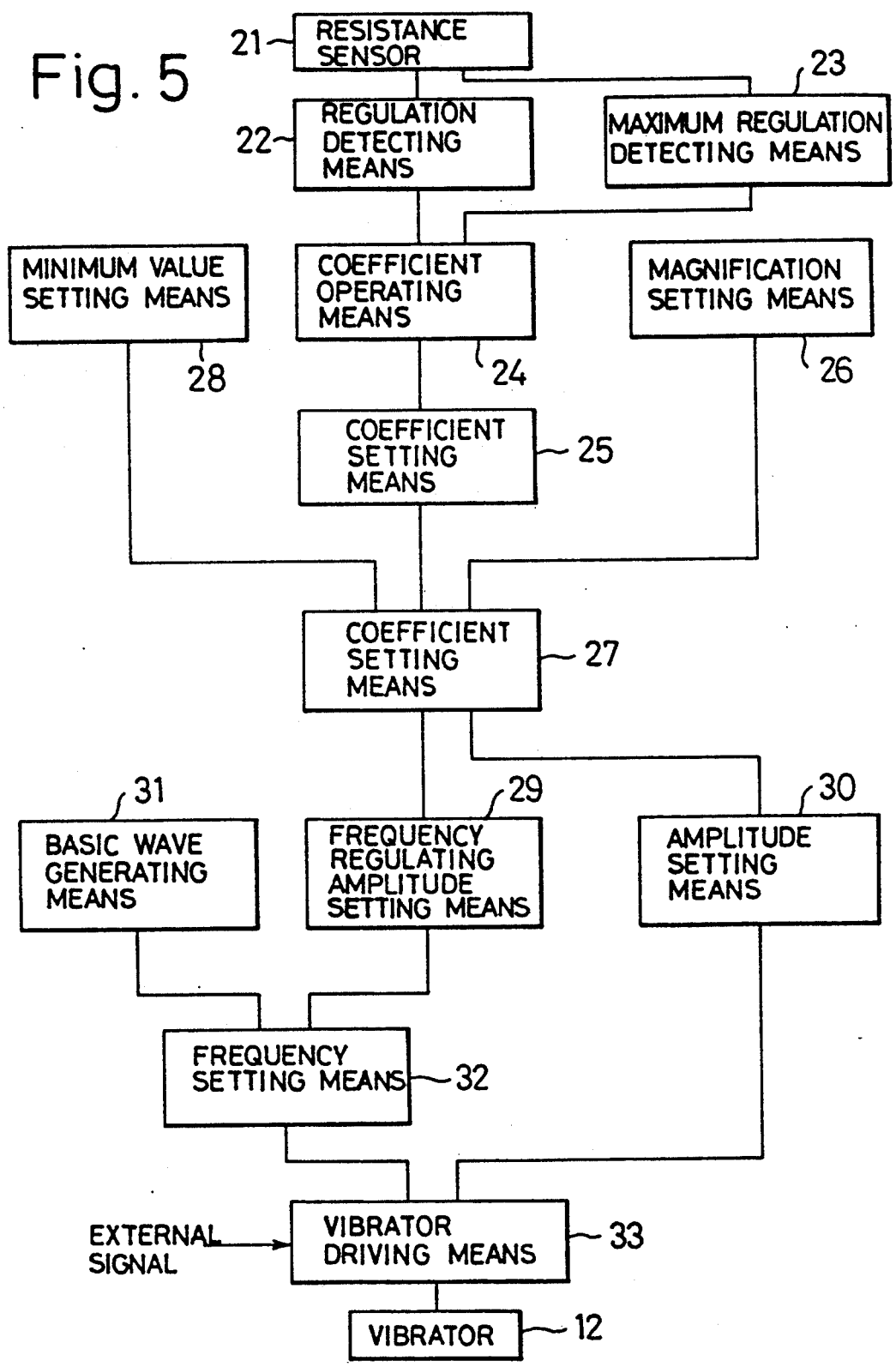

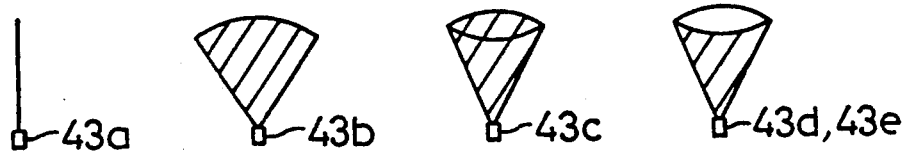
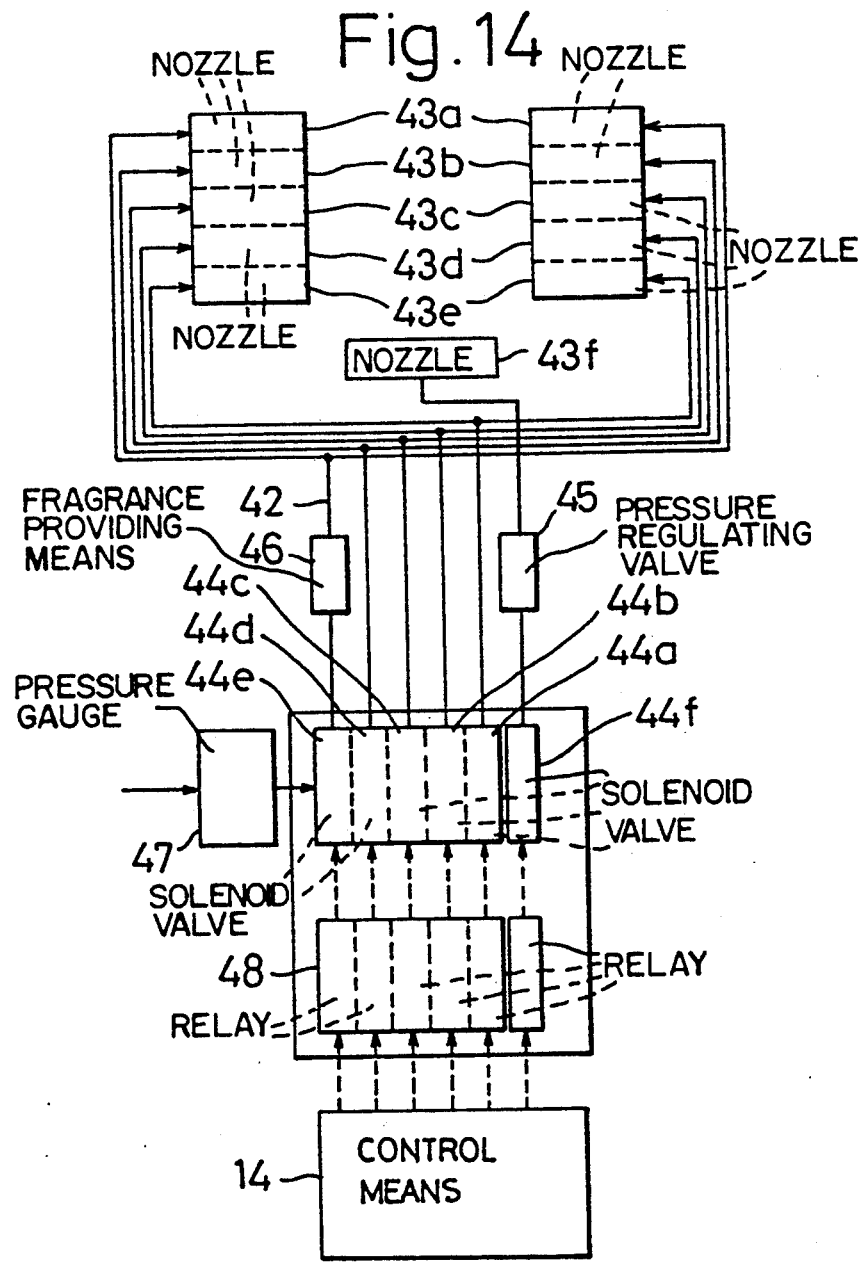

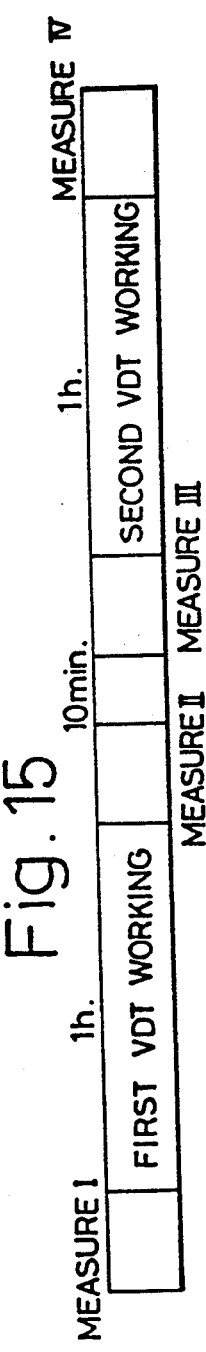
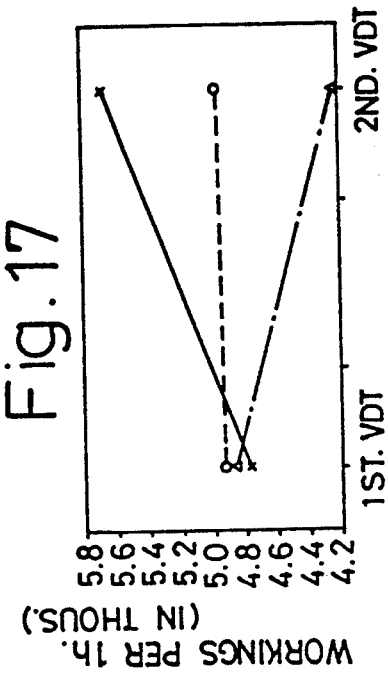
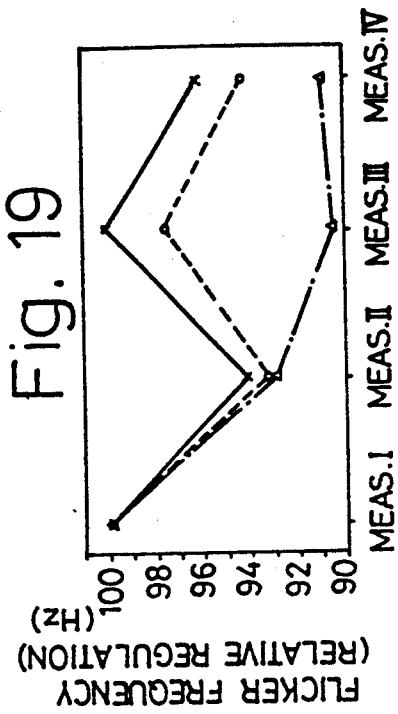
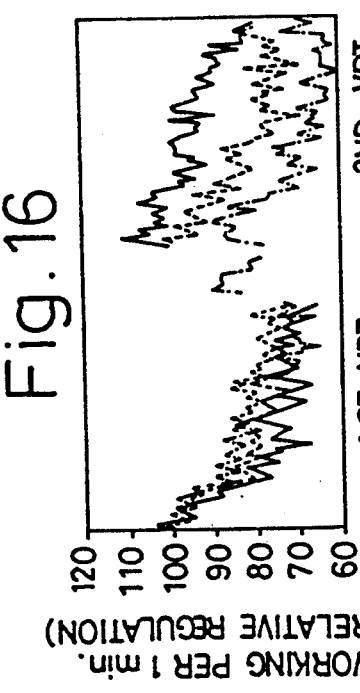
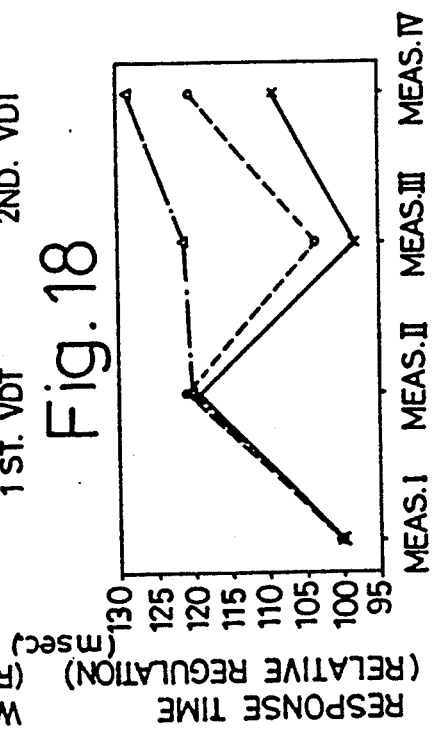

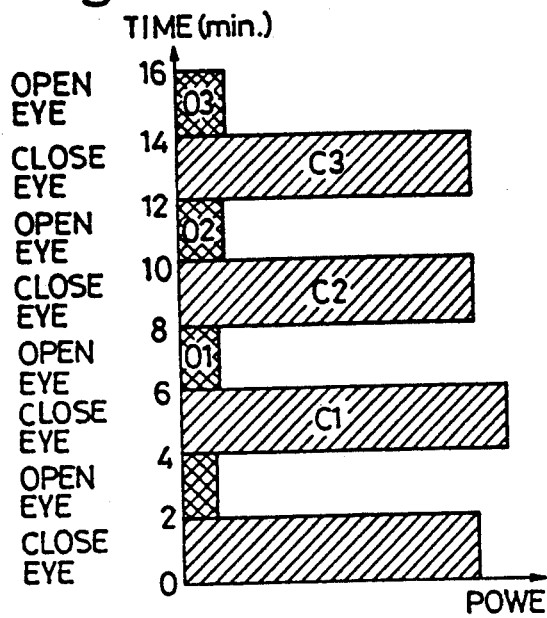
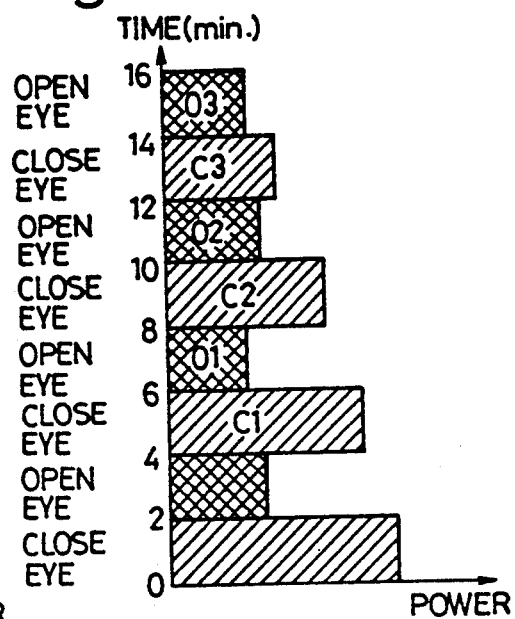
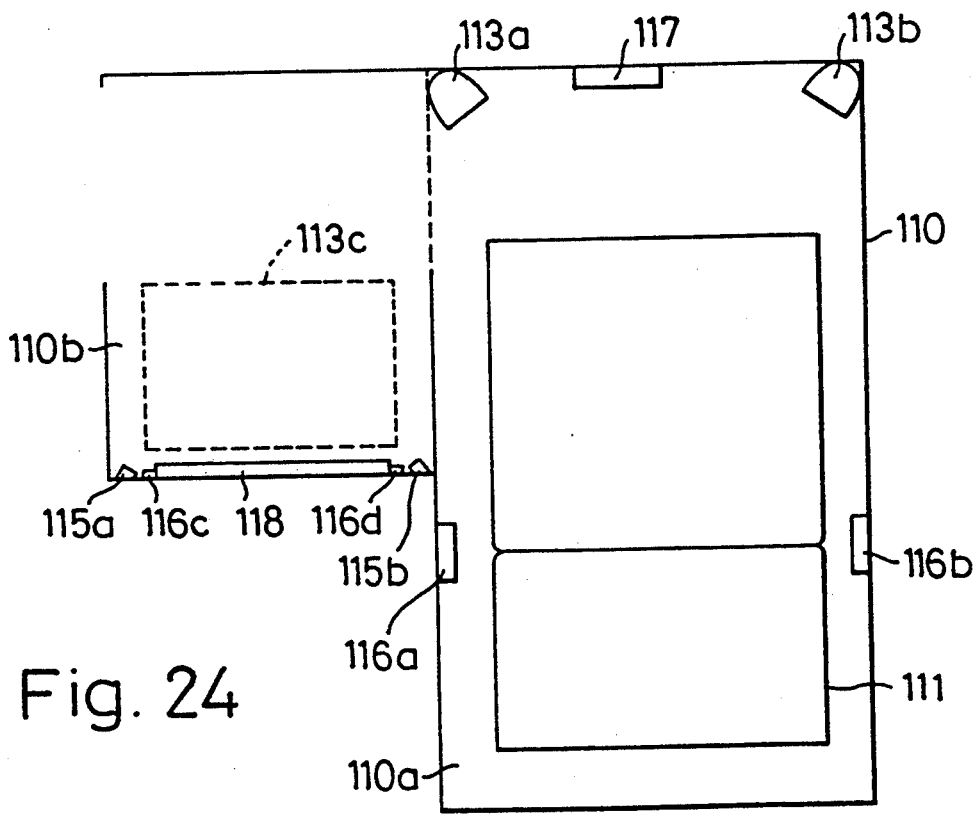

STRESS DISSOLVING REFRESHMENT SYSTEM

BACKGROUND OF THE INVENTION

1. Field of the Invention

This invention relates to a stress dissolving refreshment system which can realize a mental refreshment by reducing mainly the user's mental feeling of fatigue in a short period.

The system of the kind referred to is useful when utilized in lowering or dissolving any mental stress accumulated during continued business or office work of the user so as to allow the user to return to the work again with a strong desire.

2. Description of Related Art

In recent office work, the mental stress is likely to be accumulated in office workers during continued operation of office machines and equipments for office automation and the like which have been widely and rapidly developed and adopted. There is now a demand to reduce such stress and refresh office workers, since it has been found that accumulatively increased mental stress causes deterioration of worker contemplative faculty or attentiveness. As a result the worker will become generally dull in and the office work will become less efficient which easily and often involve clerical error and so on.

Japanese Patent Application Laid-Open Publications Nos. 61-220653 and 62-38162, by H. Hagiwara et al disclose that stress dissolving devices. The devices are a chair, bed or the like having portions engageable with back and waist parts of the user which are equipped with a plurality of vibrately members separate vertical and horizontal arrays as mutually separated so that they will be actuated to produce a vibration pattern which varies in time on the basis of, for example, an undulatory phenomenon existing in the natural world. The user on the chair or bed is exposed to an optimum vibration for dissolving the user's mental feeling of fatigue. In another Japanese Patent Application Laid-Open Publication No. 63-283641, K. Araki at al have further suggested the use of electric resistance of skin as a measure denoting the degree of mental relaxation caused by vibration. The electrical resistance of skin in initial stage of use is detected at the user's finger tips where the maximum regulation of such resistance is assumed. The resistance is detected at predetermined time intervals and the vibration intensity is controlled in accordance with the degree of relaxation represented by such detection.

In still another Japanese Patent Application Laid-Open Publication No. 62-87168 of I. Mihara et al, a brain wave induction system is disclosed. The system detects fundamental wave of α-wave in the human brain waves and generates an output signal of a frequency slightly lower or higher than the detected fundamental wave. The user's sense of sight is stimulated by the output signal in an attempt to reduce the user's mental stress or to provide a mental relaxation.

According to the foregoing known systems, stress reduction to some extent has been achieved. On the other hand, there is still a need that, after the relaxation achieved by the reduction of stress, the level of the user's consciousness be elevated to attain effectively a mental refreshment. In this respect, the known systems do not elevate the consciousness level after the stress reduction. Thus, the known systems possess problems in that either that the consciousness level is suddenly enhanced after the use of the system or a rather long time is required for reaching an adequate consciousness level enough for carrying out normal office work.

SUMMARY OF THE INVENTION

A primary object of the present invention is, therefore, to provide a stress dissolving refreshment system which can effectively elevate the user's level of consciousness by providing to the user a stimulation for the refreshment after removal of tense feeling and reduction of the stress of the user.

Another object of the present invention is to provide a stress dissolving refreshment system which allows the user to quickly return to the work after the use of the system, through a smooth elevation of the level of the user's consciousness after the stress reduction, and avoiding sudden enhancement of the consciousness level or excessively long time periods required to achieve a normal consciousness level.

According to the present invention, the objects can be realized by a stress dissolving refreshment system which comprises a relaxed state induction means for providing to the user a stimulation which reduces the user's stress and leads the user to a relaxed state during a relaxing period, a refresh stimulus means for providing to the user a stimulation to elevate the level of the user's consciousness during a refreshing period which including a disillusion period following the relaxing period, and a control means for actuating the relaxed state induction means and thereafter the refresh stimulus means, wherein after the actuation of the relaxed state induction means during the relaxing period for inducing the user to the relaxed state, said control means actuates the refresh stimulus means so as to generate a weak stimulation during the disillusion period for gradually elevating the level of the user's consciousness and thereafter to generate a strong stimulation during remaining part of the refreshing period for elevating the level of the consciousness to a level good enough for allowing the user to immediately return to normal work.

Other objects and advantages of the present invention shall be made clear in following description of the invention with reference to preferred embodiments shown in accompanying drawings.

BRIEF DESCRIPTION OF THE DRAWINGS

FIG. 5 is a block diagram of a vibration control section employed in the system of FIG. 1;

FIGS. 13(a) through 13(d) are diagrams illustrating air discharge pattern from the air blower in the system of FIG. 1;

FIG. 14 is an explanatory view for air feed controlling means in the system of FIG. 1;

FIG. 15 is an explanatory view for an experiment showing the effect of use of the system in FIG. 1;

FIGS. 16 to 19 show the effect of the system of FIG. 1 with numbers of working per 1 minute, total working per 1 hour, response time and flicker frequency, respectively, in contrast to mere rest and continuation of the work;

FIGS. 22a and 22b are graphs showing power spectrums respectively at refreshed and vague states;

FIG. 24 is a schematic view in another embodiment of the system according to the present invention.

Figure 1:
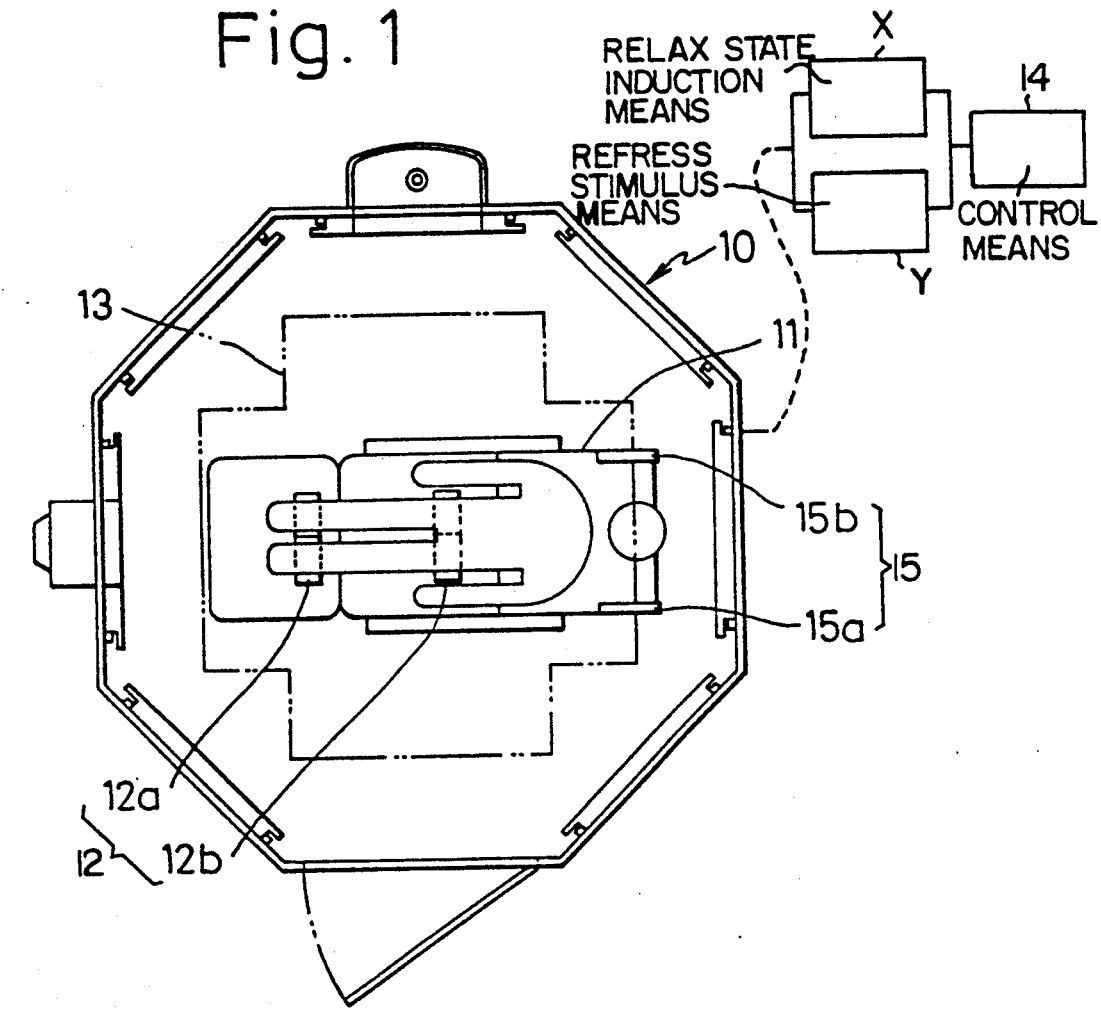
FIG. 1 shows in a schematic plan view the interior of an activation booth in an embodiment of the stress dissolving refreshment system according to the present invention.

While the present invention shall now be explained in the followings with reference to the embodiments shown in the drawings, it should be appreciated that the intention is not to limit the invention to the embodiment shown but to rather include all alterations, modifications and equivalent arrangements possible within the scope of appended claims.

DETAILED DESCRIPTION OF THE PREFERRED EMBODIMENTS

Referring to FIG. 1, there is shown an activation booth 10 used in the stress dissolving refreshment system according to the present invention. Activation booth 10, shielded both from light and sound, is provided therein with a reclining chair 11 on which the user can be seated and is arranged for providing to the user on the chair 11 one or more of stimulation by means of vibratory motion, sound, light, fragrance or air stream.

Figure 2:
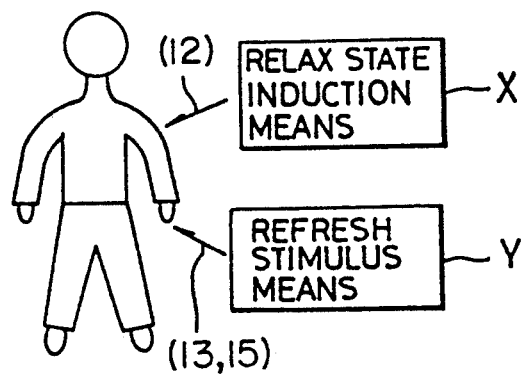
FIG. 2 is a conceptual diagram showing the system of FIG. 1.

More specifically, as shown in FIG. 2, a relaxed state induction means X is first actuated with respect to the user P seated on the reclining chair 11 in the activation booth 10 so as to slacken the tension of the user P and reduce the stress of the user P, and thereafter a refresh stimulus means Y is actuated so as to gradually elevate the level of consciousness of the user. In this case, it is preferable that the relaxed state induction means X is provided for applying a vibratory stimulation by means of a vibrator mounted mainly to the reclining chair 11, and the refresh stimulus means Y is provided for applying stimulations mainly of light and air stream. In total duration of use of the activation booth 10 which is preferably 10 to 20 minutes, an initial part of several minutes is made as a relaxing period for which the relaxed state induction means X is actuated, and a remaining part of the duration is made as a refreshing period in which the refresh stimulus means Y is actuated. Further, the refreshing period is made to include a disillusion period forming an initial part of the refreshing period in which a weak stimulation is applied by the refresh stimulus means Y, while following and remaining part of the refreshing period is utilized to apply a strong stimulation also by the refresh stimulus means Y. Assuming here that the duration of use of the activation booth 10 is set to be, for example, 10 minutes, the relaxing period may be set to last for six minutes, the disillusion period for one minute, and the remaining part of the refreshing period for three minutes.

Figure 3A:
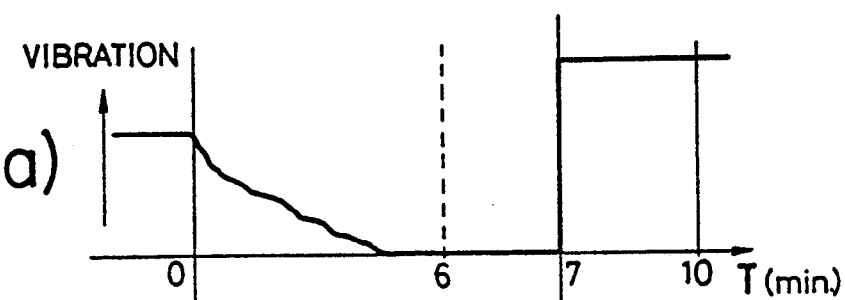
FIGS. 3(a) through 3(d) are diagrams illustrating the variation in various stimulation and activation employed in the system of FIG. 1.
Figure 4A:
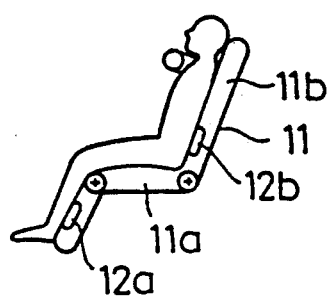
FIGS. 4a to 4c are explanatory views for the operation of a reclining chair in the system of FIG. 1.

In practical use, the user is seated on the reclining chair 11 and a starting switch (not shown) is operated, the vibrator 12 mounted to the reclining chair 11 provides such a vibration as shown in FIG. 3(a), an illuminating means 13 provided dimmably to the ceiling of the booth 10 is decreased in its illumination output, and the interior of the booth 10 is gradually darkened. When the user is thus seated on the reclining chair 11, it is made possible that a backrest 11b of the chair 11 is rotated with respect to a seat 11a of the chair 11 from a position as in FIG. 4a in which upper half of the user's body is substantially erected to a position as in FIG. 4b in which the upper half of the user's body is laid substantially horizontally, so that the user can be easily slackened in the tension to be induced into relaxed state. An attenuating stimulation by means of the vibrator 12 is to be given as will be detailed later, so that the stimulation will be gradually attenuated in response to relaxed extent of the user, while the illuminating means 13 is controlled so that a state of being lighted off will be reached in about five seconds after turning on of the starting switch. Accordingly, it is possible to increase the user's relaxed extent by applying to the user a vibratory stimulation which is gradually attenuated in a state where no photostimulation is applied as has been referred to.

Figure 3B:
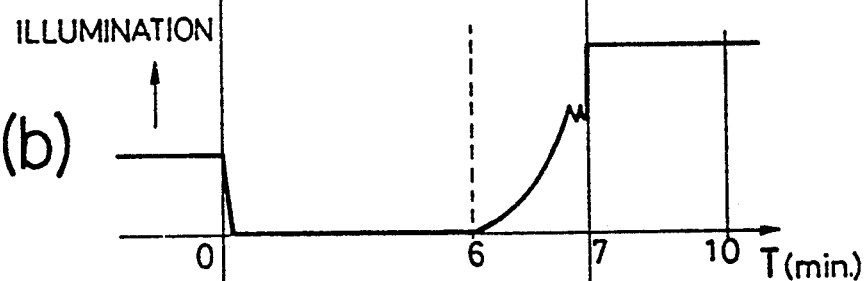

While the user is to be disillusioned to be refreshed upon termination of the relaxing period, a sudded enhancement of the level of consciousness by means of a sudden stimulation should result in a so called "surprised state" improperly, and the disillusion period is set to be at initial part of the refreshing period, during which disillusion period the intensity of the stimulation by means of the refresh stimulus means Y is gradually increased so that the level of the user's consciousness will be gradually elevated. That is, as shown in FIG. 3(b), the illuminating means 13 is so designed that its illumination is gradually increased to recover the illuminance measured adjacent the user to be several hundred lx upon termination of the disillusion period. When such predetermined illumination is recovered, further, the illuminating means 13 is made to be repeatedly flashed at a cycle of one second, and this repeated flashing of the illuminating means 13 should preferably be changed over in the illumination between, for example, 500 lx and 10 lx. At the same time, an air stream of gradually increased flow rate is applied to the user during the disillusion period so that the disillusion will be made effective. In order that the level of the user's consciousness will not be suddenly enhanced, at this time, the air stream is kept at a level of room temperature.

Figure 4B:
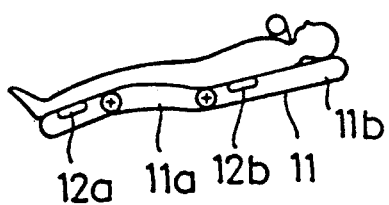
Figure 4C:
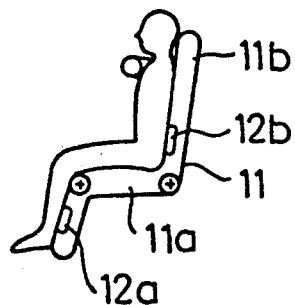

As the disillusion period terminates, the backrest 11b of the reclining chair 11 is rotated to a position of being erected with respect to the seat 11a as shown in FIG. 4c from the foregoing position of FIG. 4b, to provide to the user a feeling of tension, and the illumination of the illuminating means 13 is increased to be about 10,000 lx.

Figure 3C:
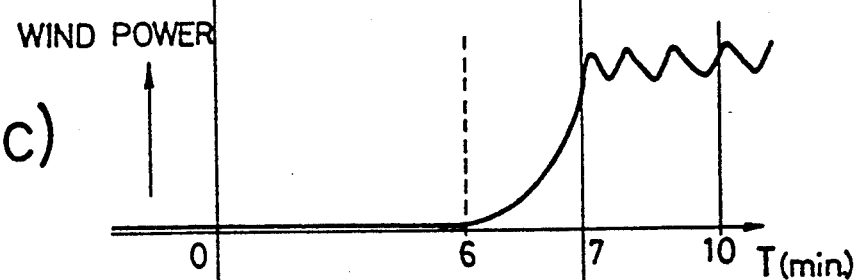

Further, the stimulation by the air stream is made higher by lowering the temperature of the air stream to apply a cool wind, or applying alternately warm and cool winds, preferably with varying flow rate, so that a strong stimulation will be given to the user, as shown in FIG. 3(c). In addition, it may be also effective to apply a stimulation of the vibratory motion at a constant intensity by means of the vibrator 12, as shown in FIG. 3(a) in the remaining refreshing period.

The vibrator 12 comprises a plurality of vibrating parts 12a, 12b ... which are shown here as opposed, for example, to calf parts of legs and waist part, the frequency and amplitude of vibration of which can be controlled individually by a vibration controller included in a control means 14 provided to the booth 10. The respective vibrating parts 12a, 12b ... are made to vary in the frequency so that the power spectrum of frequency fluctuation will be reverse proportional to the Fourier frequency, and a so called 1/f fluctuation will be provided.

In this case, the vibration amplitude of the vibrator 12 should preferably be controlled on the basis of an output of a resistance sensor 21 mounted so such proper body part of the user as a finger tip to detect and provide as the output the electrical skin resistance SRL (refer to FIG. 5). The electrical skin resistance is to vary in response to relaxed extent of the user, and the vibratory motion of properly varied amplitude in accordance with the relaxed extent of the user by carrying out a feedback as will be detailed later.

Referring here more in detail to the vibration controller in the control means 14, the output of the resistance sensor 21 is subjected to a sampling at a fixed cycle of, for example, three seconds and, as shown in FIG. 5, provided as an input concurrently to a regulation detecting means 22 for detecting a regulation from initial stage value and to a maximum regulation detecting means 23 for assuming the maximum regulation in the electrical skin resistance on the basis of the resistance measures at initial stage. The amplitude regulation of the vibrator 12 can be set in correspondence to the regulation of the electrical skin resistance. Since the regulation R of the electrical skin resistance involves an individual difference, the amplitude regulation A set to be A=kR (k being a feedback coefficient) will cause the amplitude regulation to be influenced by the individual difference so as not to allow the optimum amplitude of the vibratory stimulation for rendering the user relaxed to be provided. In the present embodiment, therefore, the control means 14 is so provided as to correct the feedback coefficient on the basis of the maximum regulation of the electrical skin resistance. On the other hand, it has been found that the maximum regulation of the electrical skin resistance is substantially proportional to the electrical skin resistance in normal state, and the maximum regulation is assumed at the maximum regulation detecting means 23 on the basis of a value of the electrical skin resistance detected for about one minute at initial state at the time when the measurement of the resistance has been started. Outputs of the regulation detecting means 22 and the maximum regulation detecting means 23 are provided to a coefficient operating means 24 to operate the feedback coefficient based on the regulation in the skin electrical resistance.

Figure 6:
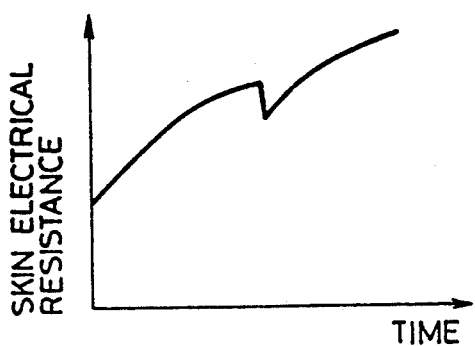
FIG. 6 is a diagram showing variation in electrical skin resistance utilized in the system of FIG. 1.

When the skin electrical resistance is suddenly reduced temporarily as seen in FIG. 6, the feedback coefficient provided as an output of the coefficient operating means 24 is made suddenly large, and the vibration amplitude of the vibrator 12 determined with such feedback coefficient employed as it is will cause a problem to arise in that the amplitude of the exciter 12 becomes suddenly large. In view of this respect, a coefficient averaging means 25 is provided for obtaining an average between the latest operated value and previously operated value of the feedback coefficient by the coefficient operating means 24. The sudden change in the feedback coefficient can be thus smoothed by the averaging of the feedback coefficient, and the vibration amplitude of the vibrator 12 can be prevented from being suddenly enlarged.

Figure 7:
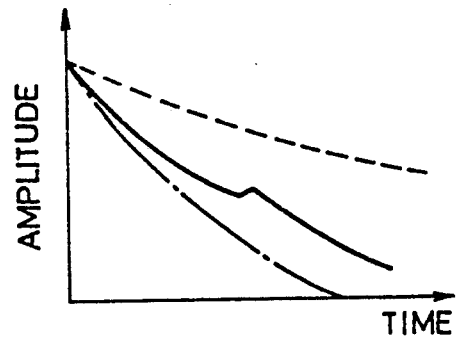
FIG. 7 is a diagram illustrating a feedback coefficient in the system of FIG. 1.

Since on the other hand the vibration amplitude of the vibrator 12 is required to be controlled for gradual reduction in rendering the user to be relaxed, it is also necessary to have the feedback coefficient gradually reduced as the time lapses after the starting. In the present instance, therefore, a magnification setting means 26 which outputs such vibration amplitude value as shown by a dotted line curve in FIG. 7 is provided for reducing forcibly the feedback coefficient as the time lapses after the starting, the output value of this means 26 is subjected to a multiplication at a coefficient setting means 27 and such feedback coefficient the value of which reduces as the time lapses from the starting as shown by a solid line curve in FIG. 7 is obtained. Further, a minimum value setting means 28 for limiting the minimum value of the feedback coefficient is provided in order to prevent the feedback coefficient based on the electrical skin resistance from being suddenly reduced so as to cause the vibratory stimulation to be not applied to the user. The minimum value is so set as to be reduced in response to the lapse of time from the starting point, as shown by a single dot chain line curve in FIG. 7, and the arrangement is so made that outputs of the minimum value setting means 28 are also provided to the coefficient setting means 27, where the feedback coefficient is so set as not to be less than the minimum value set at the means 28 in accordance with the lapse of time from the starting point.

Figure 8:
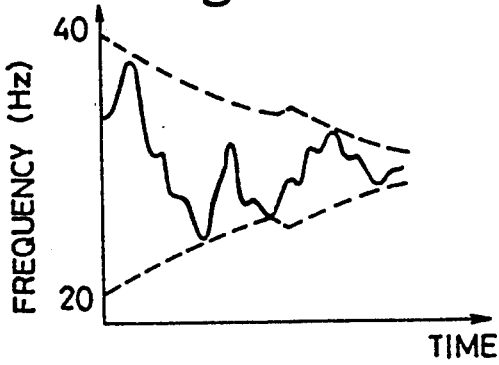
FIG. 8 is a diagram illustrating a frequency varied in response to the feedback coefficient in the system of FIG. 1.

An output of the practical feedback coefficient from the coefficient setting means 27 is input to both of means 29 for setting amplitude of vibratory frequency regulation and means 30 for setting an amplitude of the vibratory motion, so that the vibratory amplitude of the vibrator 12 is set at the amplitude setting means 30 in correspondence to the feedback coefficient, and output level of this amplitude setting means 30 is gradually attenuated in accordance with the relaxed extent of the user. At the means 29 for setting the frequency regulation amplitude, the extent to which the vibratory frequency of the vibrator 12 varies is made to vary in accordance with the feedback coefficient, as shown in FIG. 8, and the frequency regulation amplitude expanded between 20-40 Hz at initial stage after the starting is gradually narrowered to be finally converged to be around 30 Hz. At this time, the vibratory frequency of the vibrator 12 is determined by inputting outputs of the frequency regulation amplitude setting means 29 and a fundamental wave generating means 30 into a frequency setting means 32. At the fundamental wave generating means 31, the vibration of the 1/f fluctuation as has been partly referred to is generated, and the frequency regulation amplitude is restricted by the output of the frequency regulation amplitude setting means 29.

The outputs of the amplitude setting means 30 and of the frequency setting means 32 are input through a vibrator driving means 33 into the vibrator 12, which is thereby made to vibrate at the predetermined frequency and amplitude. Consequently, as shown in FIG. 3(a), the vibratory stimulation which is gradually weakened as the time lapses can be applied to the user during the relaxing period, with the intensity fitted to the relaxed extent of the user. In the refreshing period, on the other hand, a proper external signal is input if required into the vibrator driving means 33 so that the vibrator 12 may provide to the user a vibratory motion at predetermined frequency and amplitude effective to be contributive to the enhancement of the level of the user's consciousness.

Figure 9:
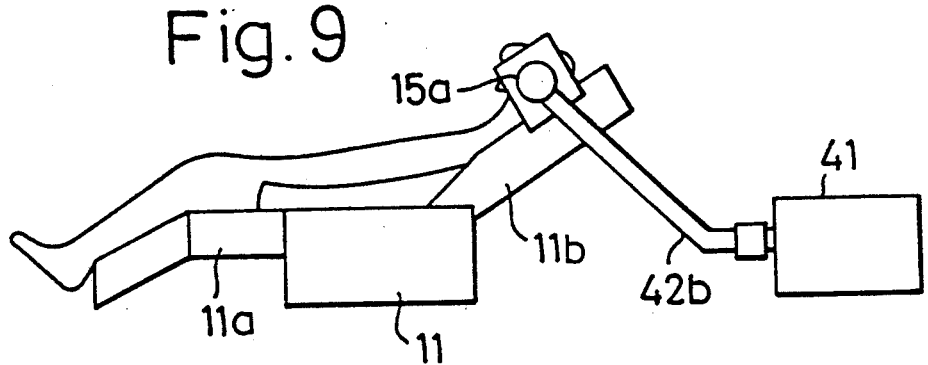
FIG. 9 is a schematic side view as magnified of the reclining chair in the system of FIG. 1.
Figure 10:
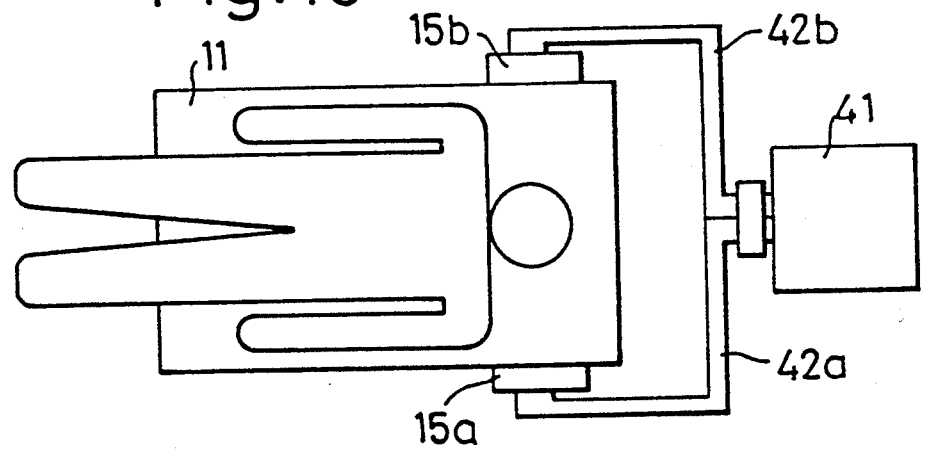
FIG. 10 is a schematic plan view as magnified also of the reclining chair in the system of FIG. 1.
Figure 11:
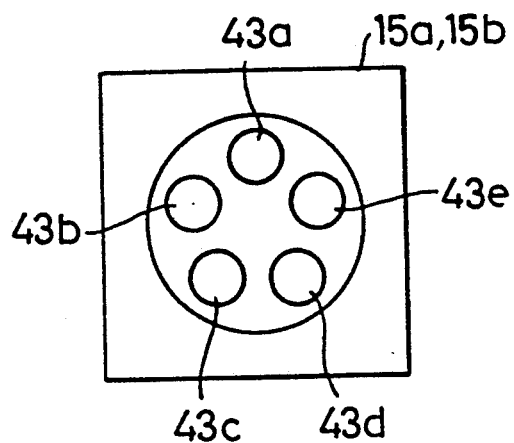
FIG. 11 shows in a front view an air blower in the system of FIG. 1.
Figure 12:
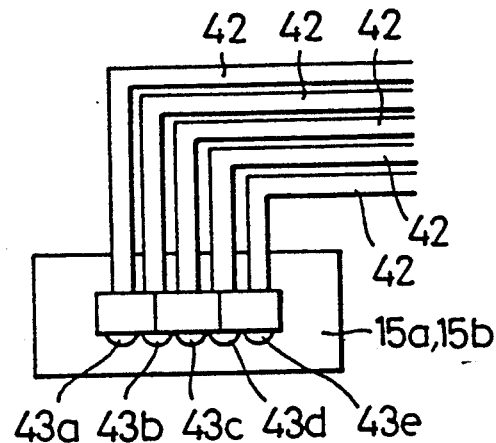
FIG. 12 is an explanatory view for air feeding pipes in the system of FIG. 1.

In the activation booth 10, further, an air-stream blowing means 15 is provided preferably to the reclining chair 11. More specifically, blowers 15a and 15b are mounted to both side edges at upper part of the backrest 11b of the reclining chair 11 as shown in FIGS. 9 and 10 and are coupled through air feeding pipes 42a and 42b to an air feeding means 41 which including an air compressor. Alternatively, the blowing means 15 may be provided on the side of the seat 11a. In concrete, the blowers 15a and 15b are respectively equipped preferably with five nozzles 43a–43e, as shown in FIGS. 11 and 12, respective ejecting ports of which are provided in mutually different shape so that discharged air-stream pattern will be, as shown in FIGS. 13(a)–13(d), linear, sector shape, solid and hollow conical shapes and so on. Between the air feeding means 41 and the respective nozzles 43a–43e of each of the blowers 15a and 15b, there are provided solenoid valves 44a–44e, as shown in FIG. 14, so that the air stream may be discharged through one or a combination of two or more of the nozzles 43a–43e by properly selectively opening the solenoid valves 44a–44e, under a blowing pressure of air stream set to be 1–7 kgl/cm$^2$. As shown by broken lines in FIG. 14, a further nozzle 43f may be provided in combination with a solenoid valve 44f and a pressure regulating valve 45 for discharging the air stream in such linear pattern as in FIG. 13(a) toward, for example, such a body part lower than the head as the scruff of neck of the user. The air stream blown out of the nozzle 43f by the pressure regulating valve 45 is maintained substantially at a constant pressure. With respect to one of the air feeding pipes 42, it is preferable to dispose a fragrance providing means 46 for having the air stream loaded with such frangrance as peppermints which having a refreshing effect, so that the level of the user's consciousness can be more effectively elevated by means of such fragrance loaded on the air stream.

Between the air feeding means 41 and the respective solenoid valves 44a–44f, there is provided a pressure gauge 47 including a regulating valve, while the solenoid valves 44a–44f themselves are provided to be openable by means of relays 48, whereby proper one or ones of the nozzles 43a–43f may be selected for the air stream discharge, and the blowing pressure of the air stream may be optimumly adjusted by controlling the pressure gauge 47 with the control means 14. According to the present embodiment, the intensity of the air stream stimulation with respect to the user can be adjusted by varying the discharge pattern or blowing pressure of the air stream, with the blowing pressure gradually increased during the disillusion period or diversely varied during the refreshing period. Further in the refreshing period, it may be possible to elevate the refreshing effect with the type of stimulation diversely varied by properly changing over the opened one or ones of the nozzles 43a–43f for the air stream discharge.

It may be also possible to provide such temperature regulating means as a heater or the like at a proper position in the air feeding pipes 42 between the air feeding means 41 and the blowing means 15, so as to vary the temperature of the air stream discharged out of the blowing means 15. It should be appreciated that the number of the nozzles may properly be increased or decreased and their shape and disposition may also be properly modified.

Figure 3D:
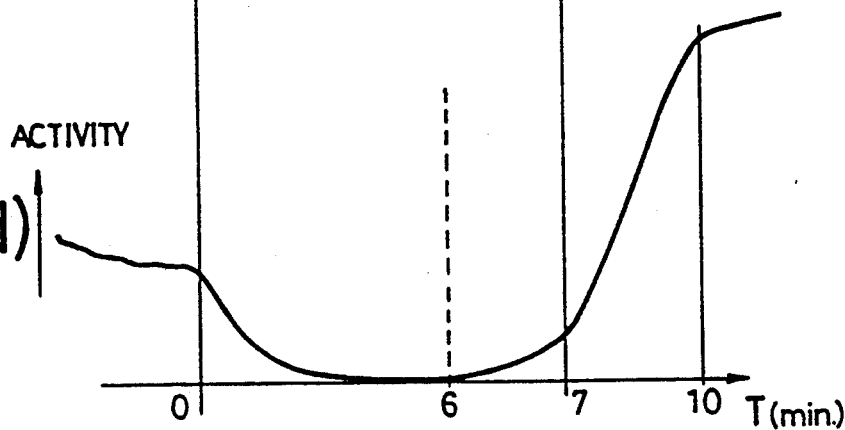

In the present embodiment as has been disclosed, the activation of the booth 10 by the user therein located allows the user induced to the relaxed state to reduce or dissolve the stress, and thereafter the user gradually elevated and then further enhanced in the level of consciousness, so as to remarkably elevate the user's activity much more than that before the use of the system, as shown by the curve of FIG. 3(d), by effectively controlling the vibration, illumination, air stream, sitting angle of the reclining seat 11 and so on.

The effect achieved by using the system according to the present invention has been empirically obtained by carrying out a measurement, VDT working and system utilization, as shown in FIG. 15. That is, a first data measurement was carried out prior to the working operation, first VDT working was carried out for one hour, and then a second measurement was made. Thereafter, the use of the refreshment system for ten minutes, a simple rest and continuous VDT workings were carried out respectively separately, thereafter a third measurement, second VDT working for one hour and then a fourth measurement were carried out. In the diagrams of FIGS. 16–19, solid line curves denote the case where the refreshment system was used, broken line curves denote the case only the simple rest was taken, and single dot chain line curves represent the case where the VDT workings have been continued. While FIG. 16 represents the working rate per 1 minute and FIG. 17 shows total working rate per 1 hour, it has been found from these drawings that the working rate attenuates in the case where the working has been continued, that the working rate does not decrease nor increase in the event where the simple rest has been taken, and that the working rate remarkably improves in the case where the refreshment system has been utilized. Further, it is appreciated from FIGS. 18 and 19 representing required response time the shorter of which the higher the activity, and flicker frequency the higher of which the higher the activity, respectively, that the user's activity is apparently made higher in the case where the refreshment system has been utilized than the cases where the simple rest has been taken and the working has been continued.

Figure 20A:
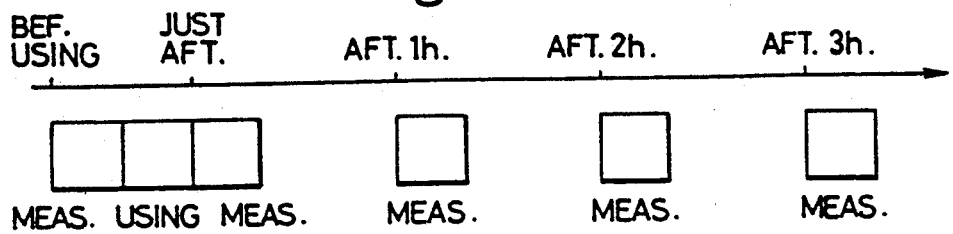
FIGS. 20a and 20b are explanatory views for the measurement of duralibity of the effect of the system of FIG. 1.
Figure 20B:
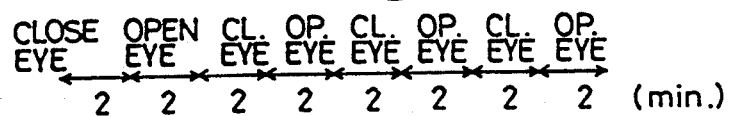
Figure 21:
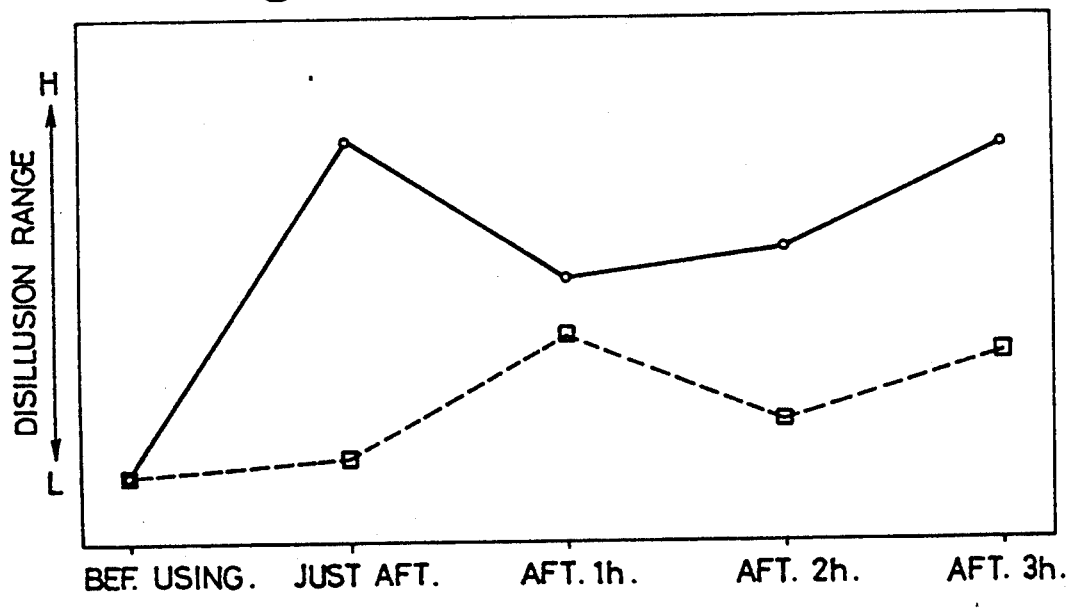
FIG. 21 is a graph showing the effect of the system of FIG. 1.

Further, in order to confirm the durability of the effect of the refreshment system utilized, such measurement as in FIG. 20a has been carried out. That is, the system was used after a first measurement, and a second measurement was carried out just after the use of the system. The measurement was thereafter repeated respectively after one hour, after two hours and after three hours. In carrying out the measurement, as shown in FIG. 20b, eye closing and opening were alternately repeated for every two minutes duration with the power spectrum of brain wave measured for 16 minutes to obtain total power spectrums of the high α-wave (10–12.8 Hz) during the eye closing and eye opening, respectively, and such results as in FIGS. 22a and 22b have been obtained, on the basis of which the activity has been calculated through a formula Activity = Total Power during Eye Closing/
Total Power during Eye Opening
= (C1 + C2 + C3)/(O1 + O2 + O3)

results of which are as shown in FIG. 21 in comparison with those in the case where the simple rest has been taken. In the drawing, a solid line curve denotes the case where the refreshment system has been used while a broken line curve denotes the case of taking only the simple rest, and it should be appreciated therefrom that the high level of activity can be maintained for a long time when the refreshment system of the present invention is used.

While in the foregoing system the vibrator 12 has been referred to as being disposed at the positions opposing the user's leg and waist parts, it may be disposed, if required, to oppose the back of the user's body. During the relaxing period, further, the system may be designed to provide to the user the white noise or such natural world sound as sea roaring, little stream murmuring or the like. Such acoustic effect elevates the relaxed extent of the user and also functions to isolate the interior of the activation booth 10 from any noise existing outside the booth. The sound volume should preferably be gradually reduced. In the case where the acoustic effect is utilized, further, it may be possible to arrange the vibrator 12 to be controlled by means of voice signals directly input thereto, or by obtaining from the voice signals such signals of predetermined frequency range as has been referred to with reference to FIG. 8.

Further, while in the foregoing embodiments the illumination of the illuminating means 13 has been disclosed to be gradually increased in the disillusion period and to be kept at a high level in the remaining refreshing period, the illuminating means 13 may also be subjected to such feedback control as has been referred to with reference to FIG. 5, by means of the output of the sensor 21 which detects the electrical skin resistance of the user during the disillusion and refreshing periods. In this case, an ideal curve of the variation with time elapsing of the consciousness level is set, and the illumination by the illuminating means 13 is adjusted while monitoring the output of the sensor 21 so that the consciousness level will be raised along such ideal curve.

Figure 23:
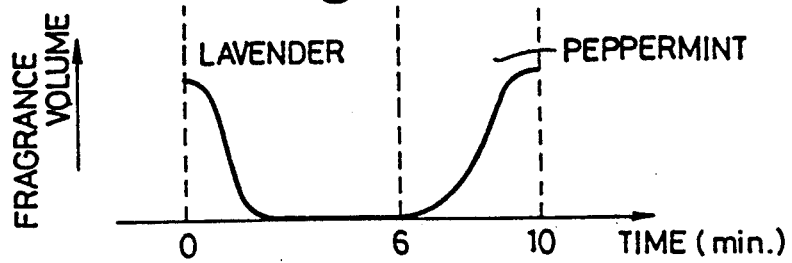
FIG. 23 is an explanatory diagram for a working aspect with a use of fragrant stimulation in the present invention.

While in the foregoing embodiment the arrangement has been referred to as providing a fragrance in the disillusion and refreshing periods by loading the fragrance on the air stream, further, it may be possible to provide a separate fragrance providing means within the activation booth 10, so that such fragrant stimulation as that of lavender which is effective to slacken the tension will be given during the relaxing period, and such other fragrant stimulation as that of peppermint effective to elevate the consciousness level will be given during the disillusion and refreshing period, in a manner as shown in FIG. 23. In this case, it is preferable that the fragrant stimulation in the relaxing period is made with the volume of fragrance gradually reduced while the stimulation in the disillusion and refreshing periods is carried out with the volume of fragrance gradually increased.

In addition, according to another feature of the present invention, there is employed an activation booth 110 in which a relaxing chamber 110a accomodating the relaxed state induction means X and a refreshing chamber 110b housing therein the refresh stimulus means Y are defined. In the present instance, the relaxed state induction means X comprising a reclining chair 111 having a vibrator, illuminating means 113a and 113b, tension-slackening fragrance means 116a and 116b, white-noise generator 117 for shielding the booth interior from the external noise and so on is provided in the relaxing chamber 110a, while in the refreshing chamber 11b the refresh stimulus means Y including an illuminating means 113c of a larger illumination, air-stream generating means 115a and 115b for providing cool air stream, fragrance providing means 116c and 116d for the generation of fragrant stimulation effective to elevate the level of consciousness of the user, and a mirror 118. The relaxing and refreshing chambers 110a and 110b are provided for being individually controllable in respect of the illumination or thermal environment, with such partition means as a curtain, door or the like interposed between them. In the present embodiment of FIG. 24, other arrangement and operation are substantially the same as those in the foregoing embodiment, including the arrangement for controlling the respective stimulations carried out in the relaxing and refreshing periods.

What is claimed is:

1. A stress dissolving refreshment system comprising a relaxed state induction means for providing to the user a stimulation which reduces the user's stress and leads the user to a relaxed state during a relaxing period, a refresh stimulus means for providing to the user a stimulation to elevate the level of the user's consciousness during a refreshing period which including a disillusion period following said relaxing period, and a control means for actuating said relaxed state induction means and thereafter said refresh stimulus means, wherein after said actuation of said relaxed state induction means during said relaxing period for inducing the user to said relaxed state, said control means actuates said refresh stimulus means so as to generate a weak stimulation during said disillusion period for gradually elevating the level of the user's consciousness and thereafter to generate a strong stimulation during remaining part of the refreshing period for elevating the level of the consciousness to a level good enough for allowing the user to immediately return to normal work.

2. The system according to claim 1 wherein said control means includes a setting control means for setting said relaxed state induction means and said refresh stimulus means where said setting control means is set to render said relaxing period and said disillusion and remaining refreshing periods to be in a ratio of 6:1:3.

3. The system according to claim 1 wherein said control means includes a setting control means for setting said relaxed state induction means and said refresh stimulus means where said setting control means is set to render the total duration of said relaxing period and said refreshing period including said disillusion period to be substantially in a range of 10 to 20 minutes.

4. The system according to claim 1 which further comprises an activation booth shielded from exterior light and noise, said relaxed state induction means and refresh stimulus means being provided within said activation booth.

5. The system according to claim 4 wherein said activation booth comprises a relaxing chamber housing therein said relaxed state induction means and a refreshing chamber housing therein said refresh stimulus means.

6. The system according to claim 4 wherein said activation booth is provided with a dimmable, illuminating means made dimmable by said control means which, during said relaxing period, gradually reducing the illumination of said illuminating means from an initial illuminance to a lighted off state which is maintained in the period, during said disillusion period, gradually increasing the illumination until said initial illuminance is reached and thereafter causing the illuminating means to repeatedly flash for a fixed time and, during said remaining refreshing period, controlling the illumination to achieve adjacent the user a sufficiently higher illuminance than said initial illuminance.

7. The system according to claim 6 wherein said initial illuminance is set to be several hundred lx, and said higher illuminance in said refreshing period is set to be more than 2,000 lx.

8. The system according to claim 4 which further comprises a reclining chain disposed in said activation booth, said chair comprising a seat on which the user is to be seated and a backrest with an adjustable angle with respect to said seat and said control means includes backrest angle control means for controlling and adjusting the angle of said backrest.

9. The system according to claim 8 wherein said backrest angle control means controls said backrest to be erected with respect to said seat at initial state, to be rotated substantially horizontal in said relaxing period and to be erected again with respect to the seat in said refreshing period.

10. The system according to claim 8 wherein said relaxes state induction means comprises a vibrator provided to said reclining chair, and said control means includes vibratory motion control means for establishing a frequency and amplitude of vibratory motion generated by said vibrator.

11. The system according to claim 10 wherein said vibrator comprises a plurality of vibrating members disposed in said reclining chair to provide said vibratory motion at least to the user's waist and leg portions.

12. The system according to claim 10 wherein said control means is provided with a sensor for detecting electrical skin resistance at fingers of the user and said vibratory motion control means establishes a variable frequency and amplitude of said vibratory motion which is varied on the basis of an output of said electrical skin resistance sensor.

13. The system according to claim 12 wherein said sensor is set to have a preliminarily set minimum value output to vary with time elapsed, said output of said sensor being maintained to be above said minimum value.

14. The system according to claim 12 wherein said control means renders said sensor to detect said electrical skin resistance at every fixed time interval and an average value of the latest detected value and previously detected value of the resistance to be employed as a current value of the resistance.

15. The system according to claim 10 wherein said control means includes a sensor for detecting electrical skin resistance at fingers of the user, and said vibratory motion control means causes said frequency and amplitude of said vibratory motion to be varied on the basis of a value of a multiplication of an output of said electrical skin resistance sensor by a preliminarily set magnification for variation with time elapsing.

16. The system according to claim 10 wherein said vibratory motion control means varies said frequency of said vibratory motion by a fluctuation of 1/f in which a fluctuation power spectrum is inversely proportional to Fourier frequency.

17. The system according to claim 10 wherein said control means renders said frequency of said vibratory motion to expand between 20–40 Hz at initial state and to gradually converge to be around 30 Hz.

18. The system according to claim 1 wherein said relaxed state induction means includes a fragrance providing means which provides to the user a fragrance to slacken the user's tension.

19. The system according to claim 1 wherein said refresh stimulus means is an air-stream blowing means for providing to the user a cool wind.

20. The system according to claim 19 wherein said blowing means includes blowers mounted to said reclining chair.

21. The system according to claim 20 wherein said blowers respectively having a nozzle for setting the shape of air stream discharged.

22. The system according to claim 20 wherein said blowing means further includes means for feeding air to said blowers and a fragrance providing means disposed between said air feeding means and said blowers for loading said cool wind with a fragrance.

23. The system according to claim 22 wherein said air-stream blowing means to vary said shape of said discharged air stream as well as an air-feeding rate of said air feeding means with time elapsed.

24. The system according to claim 1 wherein said refresh stimulus means includes means for providing a fragrance to elevate said level of the user's consciousness.

* * * * *

UNITED STATES PATENT AND TRADEMARK OFFICE
CERTIFICATE OF CORRECTION

PATENT NO. : 5,024,650

DATED : June 18, 1991

INVENTOR(S) : Hagiwara et al

It is certified that error appears in the above-identified patent and that said Letters Patent is hereby corrected as shown below:

Column 11, line 19, change "chain" to --chair--;

Column 11, line 32, change "relaxes" to --relaxed--;

Signed and Sealed this

Eighth Day of December, 1992

Attest:

DOUGLAS B. COMER

*Attesting Officer*  *Acting Commissioner of Patents and Trademarks*